United States Patent [19]

Johnson et al.

[11] Patent Number: 4,463,193

[45] Date of Patent: Jul. 31, 1984

[54] PRODUCTION OF NONCYCLIC POLYALKYLENE POLYAMINES

[75] Inventors: Thomas A. Johnson, Orefield; Michael E. Ford, Center Valley, both of Pa.

[73] Assignee: Air Products and Chemicals, Inc., Allentown, Pa.

[21] Appl. No.: 515,314

[22] Filed: Jul. 19, 1983

[51] Int. Cl.³ .............................................. C07C 85/06
[52] U.S. Cl. ..................................................... 564/479
[58] Field of Search ........................................ 564/479

[56] References Cited

U.S. PATENT DOCUMENTS

| | | | |
|---|---|---|---|
| 2,033,866 | 3/1936 | Schrauth | 564/479 X |
| 2,073,671 | 3/1937 | Andrews | 564/479 |
| 2,085,785 | 7/1937 | Bottoms | 564/479 X |
| 2,529,923 | 11/1950 | Dickey et al. | 564/479 X |
| 3,152,187 | 10/1964 | Coyne et al. | 564/479 |
| 3,211,667 | 10/1965 | Coyne et al. | 564/479 X |
| 3,320,318 | 5/1967 | Riggs et al. | 564/479 X |
| 3,714,259 | 1/1983 | Lichtenwalter et al. | 564/479 X |
| 3,755,447 | 8/1973 | Klemann et al. | 564/479 X |
| 3,766,184 | 10/1973 | Johansson et al. | 564/479 X |
| 3,767,709 | 10/1973 | Fenton | 564/479 X |
| 4,036,881 | 7/1977 | Brennan et al. | 564/479 X |
| 4,044,053 | 8/1977 | Brennan et al. | 564/479 X |
| 4,316,840 | 2/1982 | Ford et al. | 564/479 X |
| 4,316,841 | 2/1982 | Ford et al. | 564/479 X |
| 4,324,917 | 4/1982 | McConnell | 564/479 X |
| 4,405,784 | 9/1983 | Wells | 564/479 X |

*Primary Examiner*—Paul F. Shaver
*Attorney, Agent, or Firm*—Michael Leach; E. Eugene Innis; James C. Simmons

[57] ABSTRACT

A process for preparing predominantly noncyclic polyalkylene polyamine compounds is disclosed wherein an alkanolamine compound is reacted with an alkyleneamine compound and ammonia or a primary or secondary amine in the presence of a catalytically effective amount of a Group IIIB metal acid phosphate at a temperature from about 175° to 400° C. under a pressure sufficient to maintain a substantial amount of the ammonia or amine in the reaction zone.

39 Claims, No Drawings

PRODUCTION OF NONCYCLIC POLYALKYLENE POLYAMINES

TECHNICAL FIELD

This invention relates to the preparation of polyalkylene polyamines, particularly noncyclic polyalkylene polyamines.

BACKGROUND OF THE INVENTION

Low molecular weight polyethylene polyamines are used in a wide variety of applications such as corrosion inhibitors, fabric softeners, lubricating oil additives, fungicides and many others. Despite the utility of polyethylene polyamines, they are currently obtained only as by-products of ethylenediamine manufactured by the reaction of ethylene dichloride with excess ammonia. Since the polyamines are by-products of ethylenediamine preparation, the supply and quality of available polyethylene polyamines are often variable. Generally, high yields of cyclic polyethylene polyamines, e.g., piperazine, aminoethylpiperazine and the like, are produced although it is the noncyclic polyamines such as diethylenetriamine, linear and branched triethylenetetramine and higher homologs that are commercially desirable. Moreover, since sodium chloride is co-produced in large quantities, separation of the products from the sodium chloride and the handling and disposal of this corrosive inorganic salt require special measures.

The prior art discloses various attempts to circumvent these difficulties and to provide controllable efficient routes to polyethylene polyamines:

U.S. Pat. No. 3,714,259 discloses the preparation of linear polyethylene amines by contacting ethanolamine with ethylenediamine compound in the presence of hydrogen and a hydrogenation catalyst. An example of a hydrogenation catalyst is nickel containing copper and chromium components. Significant amounts of water are included in the feedstock, namely 25-50 wt % based on the combined starting ethylenediamine and monoethanolamine.

U.S. Pat. No. 3,766,184 discloses the reductive amination of monoethanolamine by a metallic catalyst of iron and nickel and/or cobalt in the presence of hydrogen.

U.S. Pat. No. 4,036,881 discloses the preparation of polyalkylene polyamines by reacting an alkanolamine with an alkyleneamine compound in the presence of a phosphorus containing substance selected from the group consisting of acidic metal phosphates, phosphoric acid compounds and anhydrides and the phosphate esters.

U.S. Pat. No. 4,044,053 is somewhat similar to the '881 patent except that the alkyleneamine compound is present in an excess amount and a diol is used in place of the alkanolamine.

U.S. Pat. No. 4,314,083 discloses a process for selectively preparing predominantly noncyclic polyalkylene polyamines by reacting an alkanolamine with an alkyleneamine compound in the presence of a salt of a nitrogen or sulfur containing substance or the corresponding acid.

U.S. Pat. No. 4,324,917 discloses ion exchange resins containing phosphonic acid functionality as catalysts for the production of polyethylene polyamines by alkylation of alkyleneamines such as ethylenediamine with alkanolamines such as monoethanolamine.

It can be seen that the prior art requires a source of preformed ethylenediamine for reaction with monoethanolamine to produce polyethylene amines. There must be a sufficient quantity of ethylenediamine present initially in the reaction mixture or a sufficient quantity continuously added to the reaction mixture in the prior art processes. Thus, production of polyethylene amines requires preparation of substantial quantities of both monoethanolamine, the alkylating agent, and ethylenediamine, the aminating agent, in separate steps and subsequent co-polymerization of the monomers to provide polyethylene polyamines. Prior art routes to polyethylene polyamines are therefore limited by their dependence on a sufficient supply of preformed ethylenediamine compared to monoethanolamine in the reactions.

SUMMARY OF THE INVENTION

It has been found that noncyclic, or linear and branched, polyalkylene polyamines are produced in good yield by reacting ammonia or a primary or secondary amine, an alkanolamine compound and an alkyleneamine compound in the presence of a catalytically effective amount of a Group IIIB metal acid phosphate at a temperature sufficient to effect reaction between the ammonia or amine, the alkanolamine compound and the alkyleneamine compound under a pressure sufficient to maintain a substantial amount of the ammonia or amine in the reaction zone.

As an advantage of the invention, the process provides predominantly noncyclic polyalkylene polyamines from mixtures of ammonia or a primary or secondary amine, an alkanolamine and an alkyleneamine with relatively little or no net consumption of the alkyleneamine. As an additional advantage, varying amounts of polyamine products may be recycled in place of the small amounts of alkyleneamine that may be consumed in polyamine formation. In this way, product slate flexibility may be increased by homologation of intermediate polyamines, such as diethylenetriamine and piperazine, to higher polyamines, such as the isomeric noncyclic and cyclic triethylenetetramine and tetraethylenepentamines. In either embodiment, compared to the alkanolamine compound, the process does not require a significant supply of an alkyleneamine as a feedstock for making the polyalkylene polyamines. By the process of the invention a substantially constant concentration of alkyleneamine may be maintained during polyamine formation.

Predominantly noncyclic polyalkylene polyamines means greater than about 50 wt % of linear and branched polyalkylene polyamines in the total polyamine product.

In the preferred embodiment, mixtures of ethylenediamine, monoethanolamine and ammonia are converted to predominantly noncyclic polyamines by a process in which a substantially constant concentration of ethylenediamine is maintained during polyamine formation. Appropriate choice of key process variables, particularly feed compositions, catalyst level in batch operation or space velocity in continuous operation, temperature and pressure, allows consumption of ethylenediamine by polyamine formation to be substantially balanced with production of ethylenediamine by amination of monoethanolamine. The process affords predominantly noncyclic polyethylene polyamines in high conversion and selectivity with less alkyleneamine consumption than would be possible in the absence of ammonia.

As a further advantage the use of Group IIIB metal acid phosphates as catalysts avoids problems associated with co-production of stoichiometric quantities of an inorganic salt.

Furthermore, in contrast to many Group IA acid phosphates, Group IIIB metal acid phosphates are insoluble in the reaction medium. Thus, under conditions for operation of this process, Group IIIB metal acid phosphates are insoluble solids that are easily localized in a fixed bed or continuous stirred tank reactor. Isolation of polyamine products, particularly in continuous processes, is therefore readily accomplished.

As an additional advantage a wide range of noncyclic polyamines is produced without the necessity of including an inert diluent in the feed and removing it from the reaction product.

DETAILED DESCRIPTION OF THE INVENTION

The invention relates to a process for synthesizing predominantly noncyclic polyalkylene polyamines, preferably linear and branched polyethylene polyamines such as diethylenetriamine and higher homologs. In the process an alkyleneamine having two amino groups and, preferably, an unbranched alkylene moiety, such as ethylenediamine, is reacted with ammonia or a primary or secondary amine, and an alkanolamine having a primary or secondary hydroxy moiety and an amino group. Preferably, the alkanolamine has an unbranched alkyleneamine moiety.

The alkanolamine compounds which are used in practicing the process include those represented by the general formula:

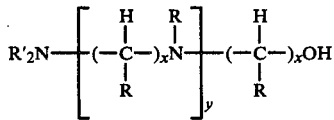

where R is hydrogen or a lower alkyl ($C_1$-$C_4$) radical, R' is hydrogen or an alkyl ($C_1$-$C_{25}$) radical, x is a number from 2 to 6, and y is a number from 0 to 3. Exemplary of suitable alkyl radicals are the lower ($C_1$-$C_4$) alkyls, such as methyl, ethyl and butyl, and higher alkyls such as octyl, decyl and octadecyl. Methyl is the preferred lower alkyl radical. However, it is preferred that R and R' be hydrogen. Thus the alkanolamine would contain a primary amino group. Examples of alkanolamine compounds that can be used are the ethanolamines, isomeric propanolamines, N-(2-aminoethyl-)ethanolamine, N-methylethanolamine, N,N-dimethylethanolamine, N,N,N'-trimethylaminoethylethanolamine and the like.

The alkyleneamine reactants that can be used in practicing the process are represented by the general formula:

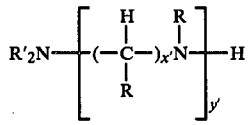

where R is a hydrogen or lower alkyl ($C_1$-$C_4$) radical, R' is hydrogen or an alkyl ($C_1$-$C_{25}$) radical, x' is a number from 2 to 6, and y' is a number from 1 to 4. Exemplary of suitable alkyl radicals are the lower ($C_1$-$C_4$) alkyls, such as methyl, ethyl and butyl, and higher alkyls such as octyl, decyl and octadecyl. It is preferred that R and R' be hydrogen. The preferred lower alkyl radical is methyl. Examples of alkyleneamine compounds suited for the reaction include 1,3-propylenediamine, N-methylpropylenediamine, 1,2-propylenediamine, diethylenetriamine, N,N,N'-trimethyldiethylenetriamine, noncyclic isomers of triethylenetetramine, noncyclic isomers of tetraethylenepentamine, N-methylethylenediamine, N,N-dimethylethylenediamine and ethylenediamine which is the preferred alkyleneamine compound.

Ammonia and the preferred primary and secondary amines which can be used in the process can be represented by the general formula

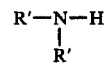

where R' is hydrogen or an alkyl ($C_1$-$C_{25}$) radical, preferably a lower alkyl ($C_1$-$C_4$) radical, such as methyl or ethyl. Proposed amine feedstocks include monomethylamine, dimethylamine, monoethylamine, diethylamine, octylamine and octadecylamine.

Noncyclic polyalkylene polyamines that are produced by the reaction of ammonia, an alkyleneamine and an alkanolamine are represented by the general formula:

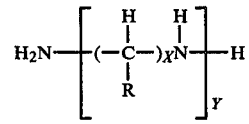

where R is hydrogen or a lower alkyl ($C_1$-$C_4$) radical, preferably a methyl radical, X is a number from 2 to 6, Y is a number from 2 to 7, and X may vary for a given value of Y. Examples of such noncyclic polyalkylene polyamines that are produced include dipropylenetriamine, tributylenetetramine, di(2-methylethylene)triamine, tri(2-methylethylene)tetramine, N-(2-aminoethyl)-1,3-propylenediamine, diethylenetriamine, and the noncyclic isomers of triethylenetetramine and tetraethylenepentamine.

Use of secondary amines instead of ammonia would lead to polyamines containing terminal dialkylamino groups. Alternatively, use of primary amines instead of ammonia would lead to polyamines which contain randomly distributed monoalkylamino groups.

One embodiment of the invention comprises a continuous process for preparing predominantly noncyclic polyalkylene polyamines by (a) adding a charge consisting essentially of ammonia or a primary or secondary amine and an alkanolamine compound to a reaction zone containing an alkyleneamine compound and a catalytically effective amount of a Group IIIB metal acid phosphate at a temperature sufficient to effect a reaction among the ammonia or amine, the alkanolamine compound and the alkyleneamine compound under a pressure sufficient to maintain a substantial amount of the ammonia or amine in the reaction zone to produce a reaction product stream containing ammonia or primary or secondary amine, alkanolamine compound, alkyleneamine compound and polyalkylene polyamines, and (b) withdrawing the product stream from the reaction zone and separating it to provide a polyalkylene polyamine stream and ammonia or the primary or secondary amine, alkanolamine compound and alkylene compound which are recycled to the reaction zone.

The invention can also be viewed as a method for substantially reducing the amount of alkyleneamine compound in the feed to the reaction zone in a continuous process for the preparation of predominantly noncyclic polyalkylene polyamines which continuous process comprises continuously adding a feed containing an alkanolamine compound and an alkyleneamine compound to a reaction zone containing a catalyst to yield a product stream comprising the polyamines, alkanolamine compound and alkyleneamine compound, separating the desired polyamines from the product stream and recycling the alkanolamine and alkyleneamine compounds to the reaction zone. The method of the invention would comprise (a) adding ammonia or a primary or secondary alkylamine to the feed to the reaction zone, (b) using a catalytically effective amount of a Group IIIB metal acid phosphate as the catalyst, and (c) effecting the reaction under a pressure sufficient to maintain a substantial amount of the ammonia or amine in the reaction zone.

To practice such a continuous process to make dialkylamino end-capped polyamines the alkanolamine compound must be reacted with the dialkylamine in the presence of an N,N-dialkylalkylenediamine, i.e., an alkyleneamine compound with one primary amino group and one tertiary amino group.

Similarly, when a monoalkylamine is substituted for ammonia, the alkyleneamine must have one primary amino group and one secondary amino group, e.g., N-methyl ethylenediamine would be used to make randomly mono-methyl substituted polyamines.

Other possibilities include the preparation of predominantly noncyclic polyamines derived from N-alkylalkanolamines. For example, the reaction of ammonia with N-methyl ethanolamine and N-methyl ethylenediamine also generates randomly methylated, although more highly methyl substituted, polyamines. However, if monomethylamine is substituted for ammonia, the polyamine becomes 100% methyl substituted, i.e., every nitrogen contains one methyl group. It should be apparent that in this and the former cases, the alkyleneamine whose concentration is to be maintained substantially constant is that which is formed by the reaction of the alkylamine or ammonia with the alkanolamine.

The catalysts which are suited for practicing the process of the invention are Group IIIB metal acid phosphates including Group IIIB metal phosphates, monohydrogen phosphates, dihydrogen phosphates and mixtures thereof. While the intent of the catalyst preparations described hereinafter was to specifically provide a particular Group IIIB monohydrogen phosphate or dihydrogen phosphate, mixtures of the Group IIIB metal phosphates of the above-mentioned types may be obtained owing to complicated dependence of the catalyst composition on preparation conditions. Nevertheless, although the Group III metal acid phosphate catalyst of the invention comprises the metal phosphate, monohydrogen phosphate, dihydrogen phosphate or mixtures thereof the monohydrogen and dihydrogen phosphates of the Group IIIB metals would be the preferred catalysts if obtainable in relatively pure form individually or in combination.

A Group IIIB metal is meant to include scandium, yttrium, lanthanum and the rare earth lanthanide metals having atomic numbers 58-71, and the rare earth actinides having atomic numbers 89 to 92.

The preferred catalysts for the production of noncyclic polyalkylene polyamines include the acid phosphates, preferably the monohydrogen phosphates and dihydrogen phosphates, of scandium, lanthanum, cerium, samarium, europium, thulium, erbium, ytterbium, yttrium, lutetium, thorium, neodymium, praseodymium, dysprosium and gadolinium.

The acid phosphate catalysts may be used for the production of polyamines either singly or in combination. As might be expected, it is preferred to use those which are more catalytically active and provide for substantial conversion to the noncyclic polyalkylene polyamine products. The preferred catalyst compounds include lanthanum monohydrogen phosphate, lanthanum dihydrogen phosphate, lanthanum phosphate, praseodymium monohydrogen phosphate, praseodymium dihydrogen phosphate, praseodymium phosphate, neodymium monohydrogen phosphate, neodymium dihydrogen phosphate, neodymium phosphate and mixtures thereof.

The quantity of the acid phosphate salts of the Group IIIB metals used in the reaction can vary widely depending upon the reactivity of the catalysts and the reactivity of the reactants present. A catalytically effective amount of material is used; in other words, an amount which causes a reaction involving ammonia or an amine, the alkyleneamine and the alkanolamine to yield noncyclic polyalkylene polyamine products at the temperature and pressure used. Usually though, the amount used to provide a catalytic effect ranges from about 0.1 to 25 mole % based upon the total amount of alkyleneamine and alkanolamine feed present in the reaction mixture, and preferably is an amount of about 0.1 to 10 mole %. Within these ranges though, the level of catalyst is empirical and is adjusted depending on the product slate desired.

In the preparation of noncyclic polyalkylene polyamines, and preferably the noncyclic polyethylene polyamines, the reaction is maintained at a temperature from about 175° C. to about 400° C., and preferably is carried out between 210° C. and 350° C. to obtain a practical rate of polyamine production without generation of excess levels of high molecular weight products.

The pressure utilized for carrying out the reaction is that pressure which is sufficient to maintain a substantial amount of the ammonia or amine in the reaction zone and may, for example, range from 10 to 350 atm in batch reactions, but preferably is that autogenous pressure which is sufficient to maintain the reaction substantially in liquid phase, although higher pressures can be used. By reaction zone is meant that vessel, e.g., autoclave, continuous stirred tank reactor or packed bed reactor, in which the catalyst is localized and production of polyamines is effected.

Although the reactions can be carried out in the batch mode, they are also amenable to continuous processes, for example operation of a continuous stirred tank reactor or a packed bed reactor. The reaction is allowed to proceed until a desired conversion is obtained or the reaction is complete. Normally the reaction is carried out within about 0.5 to 5 hours in the batch mode or residence times (based on alkanolamine and alkyleneamine components) of 0.01 to 4.0 hours in a continuous mode for practical levels of polyamine production. For continuous reactions, such as those carried out at controlled pressures in a fixed bed reactor or in a continuous stirred tank reactor, the pressure utilized for the reaction may range from 1 to 150 atm, but preferably is that pressure which is sufficient to maintain a substantial amount of the ammonia or amine in the reaction zone.

Failure to retain a substantial amount of the ammonia or amine in the reaction zone in either batch or continuous process will lead to high net consumption of alkyleneamine, owing to low production of the alkyleneamine by the amination of the alkanolamine. Reaction pressure must be sufficiently high, preferably at least 75 psig, to maintain a significant portion of the ammonia or lower alkyl amine in the reaction zone. Preferred reaction times and catalyst levels depend on catalyst reactivity and are adjusted empirically. Thus, for example, relatively lower catalyst incorporations and shorter reaction times are preferred for the production of polyamines with more reactive catalysts.

Generally, the mole ratio of alkyleneamine compound to alkanolamine compound may range from about 0.5:1 to 12:1, and preferably is about 0.75:1 to 10:1. It is advantageous in carrying out the process that the proportion of alkyleneamine compound to alkanolamine compound be in a molar ratio of at least about 0.75:1 in order to obtain the advantage of the invention in which a substantially constant concentration of alkyleneamine is maintained during polyamine formation. When the alkyleneamine compound approaches a 0.75:1 molar ratio with the alkanolamine, or falls below that level, the alkanolamine may have a tendency to form the cyclic amine compositions although the addition of ammonia or an amine as a reactant greatly diminishes this tendency.

With respect to the amount of ammonia or amine present in the reaction mixture the molar quantity of ammonia or amine may range from about 0.25:1 to 15:1 with respect to total alkyleneamine compound and alkanolamine compound, and preferably is about 0.75:1 to 10:1 although large excess quantities of ammonia or amine can be used.

It is preferred when reacting ethylenediamine (EDA) and monoethanolamine (MEA) with ammonia that the mole ratios be in a range of 0.75-10:0.5-2:0.35-20 (EDA:MEA:NH$_3$).

Recovery of the polyalkylene polyamines from the reaction mixture can be accomplished by conventional techniques, these techniques generally involving a distillation. Often a small amount of a salt, such as the one used as the catalytic material, is added to the polyalkylene polyamine separation purification as described in U.S. Pat. No. 3,755,447.

The catalysts used in the process of the invention can be prepared by the precipitation of the desired metal acid phosphate salt, washing to remove inorganic coproducts, and drying. Optionally, dried catalysts may be further processed prior to use for polyamine manufacture. Such processing is well known to those skilled in the art and may include extrusion or pelletizing, or compounding with an inert support such as alpha-alumina. Preparation of two lanthanum acid phosphates are illustrative of the general procedure by which these catalysts are made.

PREPARATION OF LANTHANUM ACID PHOSPHATE CATALYSTS

Catalyst A

Lanthanum nitrate hexahydrate (130 g, 0.30 mole) was dissolved in deionized water (150 ml) with stirring. Diammonium hydrogen phosphate (79.2 g, 0.60 mole) was dissolved in deionized water (140 ml) with stirring. While a solution of diammonium hydrogen phosphate was vigorously stirred, the solution of lanthanum nitrate was added in one portion over a period of 5 to 10 seconds. A thick, lumpy precipitate formed immediately. After 10 minutes of manual stirring, a thick, creamy suspension resulted. Vacuum filtration to isolate the precipitate was started within one-half hour of the time of addition of the solutions. Complete separation of the filtrate required 5 to 6 hours, owing to the very finely divided nature of the precipitate. The resulting pasty solid was washed sequentially with three 100 ml portions of deionized water. After washing, the filter cake was dried at 80°–90° C. to constant weight to afford 113 g of a lanthanum acid phosphate (Catalyst A).

Catalyst B

The above procedure was repeated using the following solutions to obtain 60 g of a second lanthanum acid phosphate (Catalyst B):

Ammonium dihydrogen phosphate—86.25 g (0.75 mole) in 300 ml deionized water.

Lanthanum nitrate hexahydrate—108.25 g (0.25 mole) in 150 ml deionized water.

The intent of the above-described lanthanum acid phosphate catalyst preparations is to provide a general procedure to prepare the desired Group IIIB metal monohydrogen phosphate or dihydrogen phosphate. However, phosphate-containing materials may be obtained which consist predominantly of the Group IIIB metal phosphate, the Group IIIB metal monohydrogen phosphate, the Group IIIB metal dihydrogen phosphate, or mixtures in varying proportions of the Group IIIB metal mono- and dihydrogen phosphate, and/or mixtures in varying proportions of any of the above Group IIIB metal acid phosphates with the Group IIIB metal phosphate. Such variations in catalyst composition may result from complicated dependence of the catalyst composition on preparation conditions, such as temperature, concentration of reagents, stoichiometry of reagents, rate and order of reagent addition, pH of preparation, duration of preparation, volume and pH of waterwash, duration of catalyst washing, and duration and temperature of catalyst drying. In any event, the Group IIIB metal acid phosphates obtained according to the general preparations described above for lanthanum acid phosphates are catalytically active as exemplified for the production of polyamines in the following examples.

The following examples which illustrate the nature of the process are not intended to limit the scope of the invention. In each example the reactions were carried out under the indicated conditions either in a stirred 300 ml autoclave under that autogenous pressure which was sufficient to maintain a significant portion of the reaction in liquid phase or in a fixed bed packed reactor. Such pressures ranged from 650 to 1600 psig, depending on the feed ratio, in the autoclave. In a fixed bed packed reactor the back pressure regulator was set within the range 200–1400 psig.

For purposes of brevity the products obtained are often abbreviated in the following Tables. The compound abbreviations are:
EDA—ethylenediamine
MEA—monoethanolamine
PIP—piperazine
AEP—aminoethylpiperazine
DETA—diethylenetriamine
TETA(NC)—triethylenetetramine (noncyclic isomers)
TETA(C)—triethylenetetramine (cyclic isomers)
TEPA(NC)—tetraethylenepentamine (noncyclic isomers)
TEPA(C)—tetraethylenepentamine (cyclic isomers)
HVY(NC)—pentaethylenehexamine and higher oligomeric polyethylene amines (noncyclic isomers)
HVY(C)—pentaethylenehexamine and higher oligomeric polyethylene amines (cyclic isomers)
AEEA—aminoethylethanolamine

EXAMPLE 1A

A mixture of monoethanolamine (45.8 g, 0.75 mole), ethylenediamine (90.3 g, 1.50 mole), and lanthanum acid phosphate Catalyst A (10.2 g) was placed in a 300 ml stainless steel stirred autoclave. The mole ratio of ethylenediamine:monoethanolamine was 2:1 and the catalyst incorporation was 7.49 wt % based on ethylenediamine and monoethanolamine. The mixture was heated to 300° C. for 2.0 hours during which time autogenous pressure of 650 psig developed. During the reaction the mixture was stirred at 2000 rpm. Analysis of the cooled reaction mixture by gas-liquid chromatography indicated substantial conversion of monoethanolamine and ethylenediamine to a mixture of predominantly noncyclic polyethylene polyamines. See Tables 1 and 2 for additional details.

EXAMPLE 1B

A mixture of monoethanolamine (24.9 g, 0.41 mole), ethylenediamine (48.3 g, 0.80 mole), ammonia (20.7 g, 0.22 mole), and lanthanum acid phosphate Catalyst A (5.8 g) was placed in a 300 ml stainless steel stirred autoclave. The mole ratio of ethylenediamine:monoethanolamine:ammonia was 1.97:1.0:2.98. The catalyst incorporation was 7.92 wt % based on ethylenediamine and monoethanolamine. The mixture was heated to 300° C. for 2 hours during which time autogenous pressure of 1600 psig developed. During the reaction the mixture was stirred at 2000 rpm.

Analysis of the cooled reaction mixture by gas liquid chromatography indicated substantial conversion of monoethanolamine and ethylenediamine to predominantly noncyclic polyamines. See Tables 1 and 2 for additional details.

Despite production of essentially equal amounts of polyamines in both Examples 1A and 1B, net molar consumption of ethylenediamine was substantially less when ammonia was included in the reaction mixture as seen in Tables 2 and 3. Conversely, net molar consumption of monoethanolamine was higher when ammonia was incorporated in the feed. The increase in monoethanolamine consumption (11.8 mole %) upon addition of ammonia closely matched the decrease in ethylenediamine consumption (10.9 mole %). Consequently, in addition to reacting with ethylenediamine to form higher polyamines, monoethanolamine also reacted with ammonia to form ethylenediamine. In this way, ethylenediamine that was used in production of higher noncyclic polyamines was replaced in situ.

TABLE 1

| Example | Catalyst | Catalyst Level (Wt %)[a] | Temp (°C.) | Time (Hr) | Mole Ratio (EDA/MEA/NH$_3$)[b] | Conversion[c] (%) | Selectivity[c] (NC)[e] | Selectivity[c] (AEEA)[f] |
|---|---|---|---|---|---|---|---|---|
| 1A | Lanthanum Acid Phosphate-A | 7.49 | 300 | 2 | 2.00/1.00/0.00 | 22 | 88 | 6 |
| 1B | Lanthanum Acid Phosphate-A | 7.92 | 300 | 2 | 1.97/1.00/2.98 | 26 | 92 | 4 |

[a]Based on monoethanolamine and ethylenediamine.
[b]Mole ratio of ethylenediamine:monoethanolamine:ammonia in the feedstock.
[c]Results are derived from analyses presented in Table 2, and are rounded off to the nearest integer.
[d]Based on unchanged monoethanolamine.
[e]Weight percent of linear and branched polyethylene amines in total polyamine product.
[f]Weight percent of aminoethylethanolamine (AEEA) in total polyamine product.

TABLE 2

| Example | EDA | MEA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|---|
| 1A | 47.94 | 19.42 | 0.98 | 0.44 | 15.58 | 4.63 | 0.00 | 0.00 | 0.00 | 0.00 | 0.00 | 1.42 |
| 1B | 55.46 | 18.24 | 0.39 | 0.41 | 18.36 | 3.94 | 0.24 | 1.39 | 0.00 | 0.00 | 0.00 | 1.03 |

Weight % of reaction components expressed on a water-free, ammonia-free, weight-normalized basis.

TABLE 3

| | FEEDSTOCK CONSUMPTION[a] | | |
|---|---|---|---|
| | | Consumption[b] | |
| Example | Feed Composition | EDA | MEA |
| 1A | No Ammonia | 24.2 | 39.4 |
| 1B | Ammonia Added | 13.3 | 51.2 |

[a]Based on recovered monoethanolamine or ethylenediamine.
[b]Calculated on a mole percent basis:
$$\text{Consumption} = \frac{\text{Moles charged} - \text{Moles Recovered}}{\text{Moles Charged}} \times 100\%$$

EXAMPLE 2

Lanthanum acid phosphate Catalyst A (10 cm$^3$ of −12 to −18 mesh particles) was charged to a fixed bed tubular reactor (18 cm$^3$ total volume) and overlaid with crushed vicor (5 cm$^3$ of −12 to −18 mesh particles). The reactor was heated to 265° C. in an insulated air oven. A mixture of ethylenediamine, monoethanolamine and ammonia (mole ratio EDA:MEA:NH$_3$ was 1:1:6.9) was passed over the catalyst at a liquid hourly space velocity of 1.5 hr$^{-1}$, based on EDA and MEA, at 1400 psig. Analysis of the cooled reaction product by gas/liquid chromatography indicated substantial production of predominantly noncyclic polyamines as indicated in Tables 4 and 5. Although a significant proportion of the monoethanolamine was consumed by formation of polyamines, net consumption of ethylenediamine was very low as evidenced by the data in Tables 5 and 6.

EXAMPLES 3–16

The general procedure of Example 2 was repeated for Examples 3–16 using the catalysts and reaction parameters as shown in Table 4. Catalysts designated as "metal acid phosphate-A" were prepared from the corresponding metal nitrate and diammonium hydrogen phosphate by the procedure exemplified above for lanthanum acid phosphate Catalyst A. Similarly, catalysts designated as "metal acid phosphate-B" were prepared from the corresponding metal nitrate and ammonia dihydrogen phosphate by the procedure exemplified for lanthanum acid phosphate Catalyst B. Analysis of the cooled reaction products of Examples 3–16 by gas/liquid chromatography indicated substantial production of predominantly noncyclic polyamines. Although a significant proportion of the monoethanolamine was consumed by formation of polyamines in each example, net consumption of ethylenediamine was very low. In fact, Examples 4, 5, 10 and 15 showed a net generation of ethylenediamine. See Tables 4, 5 and 6.

EXAMPLE 17

The general procedure of Example 2 was repeated with lanthanum acid phosphate B supported (16 wt % catalyst incorporation) on a low surface area macroporous inert alumina carrier (5 cm$^3$ of $-12$ to $-18$ mesh particles) overlaid with crushed vicar (5 cm$^3$ of $-12$ to $-18$ mesh particles). The reactor was heated to 255° C. A mixture of ethylenediamine, monoethanolamine and dimethylamine (mole ratio EDA:MEA:DMA was 2:1:12) was passed over the catalsyt at a liquid hourly space velocity of 7.36 hr$^{-1}$, based on total feed, at a pressure of 300 psig. Analysis of the cooled reaction product by gas/liquid chromatography indicated substantial production of N,N-dimethylethylenediamine and predominantly noncyclic polyamines as indicated in Tables 4 and 5. Although a significant proportion of the monoethanolamine was consumed by formation of polyamines, net consumption of ethylenediamine was low as evidenced by the data in Tables 5 and 6.

TABLE 4

| Example | Catalyst | LHSV (hr$^{-1}$)$^a$ | Temp (°C.) | Press. (psig) | Mole Ratio (EDA/MEA/NH$_3$)$^b$ | Conversion$^c$ (%)$^d$ | Selectivity$^c$ (NC)$^e$ | (AEEA)$^f$ |
|---|---|---|---|---|---|---|---|---|
| 2 | Lanthanum Acid Phosphate-A | 1.5 | 265 | 1400 | 1/1/6.9 | 43 | 83 | 7 |
| 3 | Lanthanum Acid Phosphate-A | 1.5 | 255 | 1400 | 1/1/6.9 | 33 | 77 | 14 |
| 4 | Lanthanum Acid Phosphate-A | 1.5 | 265 | 1400 | 2/1/6.9 | 30 | 92 | 5 |
| 5 | Lanthanum Acid Phosphate-A | 1.5 | 255 | 1400 | 1/1/4.6 | 27 | 78 | 19 |
| 6 | Lanthanum Acid Phosphate-B | 1.5 | 255 | 300 | 2/1/12 | 42 | 72 | 2 |
| 7 | Lanthanum Acid Phosphate-B | 1.5 | 245 | 300 | 2/1/12 | 29 | 71 | 5 |
| 8 | Praseodymium Acid Phosphate-A | 1.5 | 255 | 1400 | 1/1/6.9 | 27 | 70 | 26 |
| 9 | Praseodymium Acid Phosphate-A | 1.5 | 255 | 1400 | 1/1/4.6 | 33 | 78 | 18 |
| 10 | Lanthanum Acid Phosphate-B | 1.0 | 225 | 300 | 2/1/12 | 17 | 67 | 14 |
| 11 | Lanthanum Acid Phosphate-B | 1.0 | 225 | 300 | 2/1/8 | 20 | 70 | 16 |
| 12 | Lanthanum Acid Phosphate-B | 3.0 | 255 | 200 | 2/1/8 | 33 | 72 | 9 |
| 13 | Lanthanum Acid Phosphate-B | 3.0 | 255 | 200 | 2/1/4 | 38 | 77 | 7 |
| 14 | Rare Earth Acid Phosphate$^g$-B | 1.5 | 255 | 300 | 2/1/12 | 38 | 74 | 8 |
| 15 | Rare Earth Acid Phosphate$^g$-B | 1.0 | 225 | 300 | 2/1/12 | 11 | 70 | 16 |
| 16 | Lanthanum Acid Phosphate-B | 1.5 | 255 | 1400 | 2/1/12 | 40 | 88 | 7 |
| 17 | Lanthanum Acid Phosphate-B | 7.4$^h$ | 255 | 300 | 2/1/12$^i$ | 32 | 68 | 5 |

$^a$Based on monoethanolamine and ethylenediamine.
$^b$Mole ratio of ethylenediamine:monoethanolamine:ammonia in the feedstock.
$^c$Results are derived from analyses presented in Table 4, and are rounded off to the nearest integer.
$^d$Based on unchanged monoethanolamine.
$^e$Weight percent of linear and branched polyethylene amines in total polyamine product.
$^f$Weight percent of aminoethylethanolamine (AEEA) in total polyamine product.
$^g$Catalyst comprised a mixture of lanthanum, cerium, praseodymium and neodymium in a 9.6:2.2:1.0:3.1 weight ratio, respectively.
$^h$Based on total monoethanolamine, ethylenediamine and dimethylamine.
$^i$Mole ratio of EDA/MEA/DMA.

TABLE 5

| Example | EDA | MEA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|---|
| 2 | 46.81 | 28.60 | 0.73 | 1.03 | 12.00 | 4.05 | 0.32 | 3.59 | 0.15 | 0.30 | 0.00 | 1.78 |
| 3 | 48.12 | 33.50 | 0.58 | 0.71 | 10.05 | 2.49 | 0.09 | 0.99 | 0.04 | 0.00 | 0.00 | 2.51 |
| 4 | 66.78 | 23.80 | 0.39 | 0.21 | 13.04 | 2.31 | 0.00 | 0.56 | 0.00 | 0.00 | 0.00 | 0.89 |
| 5 | 50.25 | 36.71 | 0.40 | 0.15 | 10.92 | 2.18 | 0.00 | 0.00 | 0.00 | 0.00 | 0.00 | 3.19 |
| 6 | 66.01 | 18.30 | 0.66 | 1.16 | 9.01 | 2.57 | 1.75 | 1.26 | 1.09 | 0.00 | 0.00 | 0.38 |
| 7 | 65.71 | 23.89 | 0.54 | 0.95 | 6.73 | 1.89 | 1.21 | 0.69 | 0.45 | 0.00 | 0.00 | 0.61 |
| 8 | 47.44 | 33.94 | 0.44 | 0.16 | 11.24 | 1.90 | 0.00 | 0.12 | 0.00 | 0.00 | 0.00 | 3.11 |

TABLE 5-continued

| Example | EDA | MEA | PIP | AEP | DETA | TETA(NC) | TETA(C) | TEPA(NC) | TEPA(C) | HVY(NC) | HVY(C) | AEEA |
|---|---|---|---|---|---|---|---|---|---|---|---|---|
| 9 | 47.01 | 36.88 | 0.29 | 0.12 | 7.22 | 1.14 | 0.00 | 0.00 | 0.00 | 0.00 | 0.00 | 3.10 |
| 10 | 67.07 | 28.11 | 0.42 | 0.91 | 3.71 | 0.67 | 0.23 | 0.00 | 0.11 | 0.00 | 0.00 | 0.91 |
| 11 | 65.28 | 27.22 | 0.36 | 0.54 | 4.25 | 0.90 | 0.12 | 0.00 | 0.00 | 0.00 | 0.00 | 1.21 |
| 12 | 65.43 | 23.20 | 0.44 | 0.78 | 6.33 | 1.68 | 0.64 | 0.17 | 0.34 | 0.00 | 0.00 | 0.99 |
| 13 | 64.42 | 21.15 | 0.57 | 0.91 | 7.74 | 2.20 | 0.52 | 1.17 | 0.29 | 0.00 | 0.00 | 1.03 |
| 14 | 66.53 | 21.28 | 0.67 | 0.84 | 7.44 | 1.39 | 0.50 | 0.16 | 0.29 | 0.00 | 0.00 | 0.92 |
| 15 | 65.20 | 29.29 | 0.32 | 0.38 | 3.62 | 0.24 | 0.09 | 0.00 | 0.00 | 0.00 | 0.00 | 0.87 |
| 16 | 60.22 | 20.28 | 0.60 | 0.30 | 13.23 | 3.08 | 0.08 | 1.00 | 0.00 | 0.00 | 0.00 | 1.48 |
| 17[a] | 64.28 | 25.27 | 0.35 | 0.69 | 5.54 | 1.27 | 0.68 | 0.29 | 0.35 | 0.00 | 0.00 | 0.54 |

Weight % of reaction components expressed on a water-free, ammonia-free, weight-normalized basis.
[a]N,N—dimethylethylenediamine was 0.73.

TABLE 6

FEEDSTOCK CONSUMPTION[a]

| Example | Feed Composition[b] | Consumption[c] EDA | Consumption[c] MEA |
|---|---|---|---|
| 2 | 1/1/6.9 | 3.19 | 43.24 |
| 3 | 1/1/6.9 | 1.18 | 33.54 |
| 4 | 2/1/6.9 | (0.23)[d] | 29.73 |
| 5 | 1/1/4.6 | (1.33)[d] | 27.20 |
| 6 | 2/1/12 | 0.23 | 41.97 |
| 7 | 2/1/12 | 0.78 | 29.24 |
| 8 | 1/1/6.9 | 5.24 | 26.81 |
| 9 | 1/1/4.6 | 4.37 | 32.65 |
| 10 | 2/1/12 | (1.27)[d] | 16.76 |
| 11 | 2/1/8 | 1.43 | 19.40 |
| 12 | 2/1/8 | 3.20 | 32.64 |
| 13 | 2/1/4 | 3.32 | 37.71 |
| 14 | 2/1/12 | 2.33 | 38.49 |
| 15 | 2/1/12 | (0.23)[d] | 11.38 |
| 16 | 2/1/12 | 9.94 | 40.03 |
| 17 | 2/1/12[e] | 12.52 | 32.29 |

[a]Based on recovered ethylenediamine or monoethanolamine.
[b]Mole ratio of ethylenediamine:monoethanolamine:ammonia.
[c]Calculated on a weight percent basis with the water-free, ammonia-free compositions of feedstock and product:

$$\text{Consumption} = \frac{\text{Weight percent charged} - \text{Weight percent recovered}}{\text{Weight percent charged}} \times 100\%$$

[d]Net generation of ethylenediamine.
[e]Mole ratio of ethylenediamine:monoethanolamine:dimethylamine.

As can be seen from the data set forth in the above Tables noncyclic polyamines were generally obtained in high selecivity, often greater than 75 wt % of the total product mixture, from this process. Diethylenetriamine was the predominant noncyclic polyamine which was produced. However, the product slate can be significantly altered by modification of the appropriate process variables. Thus, at a fixed temperature, pressure and space velocity, reduction of the ethylenediamine:monoethanolamine molar feed ratio from 2:1 to 1:1 as shown in Examples 2 and 4 resulted in the production of a wider range of noncyclic polyamines with little loss of selectivity.

To maintain the desired product slate, Examples 2 and 3 indicate that careful control of reaction temperature is necessary. At a fixed pressure, space velocity and EDA:MEA feed ratio, reduction of reaction temperature from 265° C. to 255° C. resulted in lower selectivity to noncyclic polyamines and higher selectivity to aminoethylethanolamine. Thus, the concentration of aminoethylethanolamine, which is a commercially valuable intermediate for preparation of nonionic surfactants and urethane catalysts, in the product stream depends strongly on, and is readily controlled by, the temperature of reaction.

In comparing Examples 6 and 7 with Examples 2-4 it can be seen that lanthanum acid phosphate-B was a more reactive catalyst than lanthanum acid phosphate-A since lower temperatures were required (at identical space velocity of ethylenediamine and monoethanolamine) to obtain high conversions of monoethanolamine. With a 2:1 ethylenediamine:monoethanolamine feed ratio, the more reactive catalyst showed somewhat lower selectivity to noncyclic polyamines. See Examples 4 and 6.

At the lower temperature and space velocity of Examples 10 and 11, lower conversions of monoethanolamine were obtained compared to Examples 2-9. Selectivity to noncyclic polyamines was comparable to that obtained under the more vigorous conditions with lanthanum acid phosphate-B (Examples 6 and 7), an indication that no major change in amination pathway had occurred. However, selectivity to aminoethylethanolamine was higher and selectivity to cyclics was lower at 225° than at 245° or 255° C. The lower rate of intramolecular cyclization of aminoethylethanolamine at 225° C. accounts for this observation.

Examples 12 and 13 demonstrate production of noncyclic polyamines over lanthanum acid phosphate-B at low reaction pressure. Furthermore, in Example 13 noncyclic polyamines were made with low consumption of ethylenediamine, good conversion of monoethanolamine and high selectivity to noncyclic polyamines with relatively little ammonia.

The use of an acid phosphate Catalyst B comprising a mixture of rare earth metals for the production of predominantly noncyclic polyamines with little or no consumption of ethylenediamine was demonstrated in Examples 14 and 15. A comparison of Example 6 with Example 14 and Example 10 with Example 15 reveals that rare earth acid phosphate Catalyst B is slightly less reactive and, consequently, more selective for the production of noncyclic polyamines under otherwise identical experimental conditions.

It is readily apparent that the process of this invention provides predominantly noncyclic polyethylene polyamines in high conversion and selectivity from mixtures of ethylenediamine or a higher noncyclic polyethylene polyamine, monoethanolamine and ammonia. With inclusion of ammonia, significant amounts of monoethanolamine are converted to ethylenediamine and, by homologation of ethylenediamine, to higher noncyclic polyamines during polyamine formation. Consequently, although ethylenediamine or a higher alkyleneamine is present as a component of the reaction mixture, this process has minimal or no dependence on a source of the preformed alkyleneamine.

In contrast to the prior art, the process of this invention not only produces predominantly noncyclic polyamines but also minimizes or eliminates the need for preformed ethylenediamine. Unexpectedly, the inclusion of ammonia or amines in reactions of monoethanolamine and ethylenediamine allows efficient production of predominantly noncyclic polyamines from ethylenediamine and monoethanolamine and in situ regeneration of ethylenediamine by amination of monoethanolamine.

STATEMENT OF INDUSTRIAL APPLICATION

The inventive process for preparing predominently noncyclic polyalkylene polyamine compounds is applicable to the preparation of noncyclic polyethylene polyamines which are extensively used in a wide variety of applications. Significant uses of polyethylene polyamines include their use as corrosion inhibitors, fabric softeners, lubricating oil additives, co-monomers for polyamide resins, fungicides, surfactants, curing agents for epoxy resins and chelating agents.

We claim:

1. A process for preparing predominantly noncyclic polyalkylene polyamines which comprises:

contacting ammonia or a primary or secondary amine with an alkanolamine compound having an amino group and a primary or secondary hydroxy group and an alkyleneamine compound having two amino groups in the presence of a catalytically effective amount of a Group IIIB metal acid phosphate at a temperature sufficient to effect a reaction among the ammonia or amine, the alkanolamine compound and the alkyleneamine compound under a pressure sufficient to maintain a substantial amount of the ammonia or amine in the reaction zone.

2. The process of claim 1 in which the Group IIIB metal is scandium, yttrium, lanthanum or a rare earth lanthanide having an atomic number from 58 to 71.

3. The process of claim 1 in which the catalyst is a Group IIIB metal monohydrogen phosphate.

4. The process of claim 3 in which the catalyst is a monohydrogen phosphate salt of lanthanum, yttrium, neodymium, cerium, praseodymium or samarium.

5. The process of claim 1 in which the catalyst is a Group IIIB dihydrogen phosphate.

6. The process of claim 5 in which the catalyst is a dihydrogen phosphate salt of lanthanum, praseodymium, neodymium, samarium, dysprosium or gadolinium.

7. The process of claim 1 in which the temperature is from about 175° C. to 400° C. and the pressure is at least 1 atmosphere.

8. The process of claim 7 in which the catalyst is a lanthanum acid phosphate.

9. The process of claim 1 in which the molar ratio of alkyleneamine to alkanolamine is from 0.5:1 to 12:1.

10. The process of claim 1 in which the molar ratio of ammonia or amine to total alkyleneamine compound and alkanolamine compound is about 0.25:1 to 15:1.

11. A process for preparing a noncyclic polyalkylene polyamine which comprises:

(a) contacting an alkanolamine compound having a primary amino group and a primary or secondary hydroxyl group of the general formula

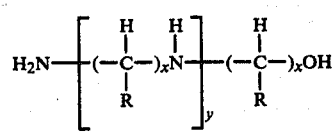

where R is hydrogen or a lower alkyl (C$_1$-C$_4$) radical, x is a number from 2 to 6, and y is a number from 0 to 3, with ammonia and an alkyleneamine compound having two primary amino groups of the general formula:

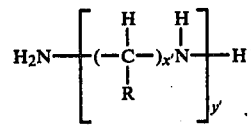

where R is hydrogen or a lower alkyl (C$_1$-C$_4$) radical, x' is a number from 2 to 6, and y' is a number from 1 to 4, in the presence of a catalytically effective amount of an acid phosphate salt of a Group IIIB metal at a temperature from about 210° C. to about 350° C. under a pressure sufficient to maintain a substantial amount of the ammonia in the reaction zone, and (b) recovering the noncyclic polyalkylene polyamine from the resultant reaction mixture.

12. The process of claim 11 in which the catalyst is an acid phosphate salt of a Group IIIB metal selected from the group consisting of scandium, yttrium, lanthanum and the rare earth lanthanides having an Atomic Number from 58 to 71.

13. The process of claim 12 in which the alkanolamine is an ethanolamine when R is hydrogen or a lower alkyl (C$_1$-C$_4$) radical, x is 2 and y is 0 to 3, and the alkyleneamine is an ethyleneamine when R is hydrogen or a lower alkyl (C$_1$-C$_4$) radical, x' is 2 and y' is 1 to 4.

14. The process of claim 13 in which the alkanolamine is monoethanolamine and the ethyleneamine is ethylenediamine.

15. The process of claim 14 in which the molar ratio of ethylenediamine:monoethanolamine:ammonia is from 0.75-10:0.5-2:0.35-20.

16. The process of claim 15 in which the catalyst is a Group IIIB metal monohydrogen phosphate.

17. The process of claim 16 in which the catalyst is a monohydrogen phosphate salt of lanthanum, neodymium or praseodymium.

18. The process of claim 15 in which the catalyst is a Group IIIB metal dihydrogen phosphate.

19. The process of claim 18 in which the catalyst is a dihydrogen phosphate salt of lanthanum, neodymium or praseodymium.

20. A process for preparing a noncyclic polyalkylene polyamine which comprises:

(a) contacting an alkanolamine compound having an amino group and a primary or secondary hydroxy group of the general formula:

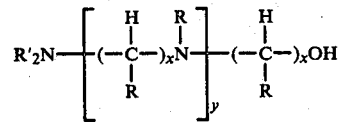

where R is hydrogen or a lower alkyl (C$_1$-C$_4$) radical, R' is hydrogen or an alkyl (C$_1$-C$_{25}$) radical, x is a number from 2 to 6, and y is a number from 0 to 3 with an alkyleneamine compound having two amino groups of the general formula:

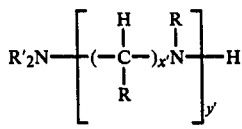

where R is a hydrogen or a lower alkyl ($C_1$-$C_4$) radical, R' is hydrogen or an alkyl ($C_1$-$C_{25}$) radical, x' is a number from 2 to 6, and y' is a number from 1 to 4 and ammonia or an amine of the general formula:

where R' is independently hydrogen or an alkyl ($C_1$-$C_{25}$) radical in the presence of a catalytically effective amount of an acid phosphate salt of a Group IIIB metal at a temperature from about 175° C. to about 400° C. under a pressure sufficient to maintain a substantial amount of the ammonia or amine in the reaction zone.

21. The process of claim 20 in which the catalyst is a Group IIIB metal monohydrogen phosphate.

22. The process of claim 20 in which the catalyst is a Group IIIB metal dihydrogen phosphate.

23. A continuous process for preparing predominantly noncyclic polyalkylene polyamines which comprises (a) adding a charge consisting essentially of ammonia or a primary or secondary amine and an alkanolamine compound having an amino group and a primary or secondary hydroxy group to a reaction zone containing an alkyleneamine compound having two amino groups and a catalytically effective amount of a Group IIIB metal acid phosphate at a temperature sufficient to effect a reaction among the ammonia or amine, the alkanolamine compound and the alkyleneamine compound under a pressure sufficient to maintain a substantial amount of the ammonia or amine in the reaction zone to produce a reaction product stream comprising ammonia or primary or secondary amine, alkanolamine compound, alkyleneamine compound and polyalkylene polyamines, and (b) withdrawing the product stream from the reaction zone and separating it to provide a polyalkylene polyamines stream and ammonia or the primary or secondary amine, alkanolamine compound and alkyleneamine compound which are recycled to the reaction zone.

24. The process of claim 23 in which the charge consists essentially of ammonia and monoethanolamine and the alkyleneamine is ethylenediamine.

25. The process of claim 24 in which the molar ratio of ethylenediamine:monoethanolamine:ammonia in the reaction zone is maintained from 0.75–10:0.5–2:0.35–20 and the pressure is from about 5 to 150 atmospheres.

26. The process of claim 23 in which the catalyst is a lanthanum acid phosphate.

27. The process of claim 25 in which the catalyst is a lanthanum acid phosphate.

28. In a continuous process for the preparation of predominantly noncyclic polyalkylene polyamines which comprises continuously adding a feed comprising an alkanolamine compound having a primary amino group and a primary or secondary hydroxy group and an alkyleneamine compound having two primary amino groups to a reaction zone containing a catalyst to yield a product stream comprising noncyclic polyalkylene polyamines, alkanolamine compound and alkyleneamine compound, separating the desired polyamines from the product stream and recycling the alkanolamine and alkyleneamine compounds to the reaction zone, the method for substantially reducing the amount of alkyleneamine compound in the feed to the reaction zone, which method comprises (a) adding ammonia or a primary or secondary alkylamine to the feed to the reaction zone, (b) using a catalytically effective amount of a Group IIIB metal acid phosphate or as the catalyst, and (c) effecting the reaction under a pressure sufficient to maintain a substantial amount of the ammonia or amine in the reaction zone.

29. The method of claim 28 in which unreacted ammonia or amine is recycled to the reaction zone.

30. The method of claim 29 in which the alkanolamine compound is monoethanolamine and the alkyleneamine compound is ethylenediamine.

31. The method of claim 30 in which the molar ratio of ethylenediamine:monoethanolamine:ammonia in the reaction zone is from 0.75–10:0.5–2:0.35–20.

32. The method of claim 30 in which the catalyst is a lanthanum acid phosphate.

33. The method of claim 32 in which the pressure is from about 5 to 150 atmospheres.

34. The method of claim 33 in which the temperature is from 175° C. to 400° C.

35. The process of claim 1 in which the catalyst is a mixture of the Group IIIB phosphate, monohydrogen phosphate and dihydrogen phosphate.

36. The process of claim 15 in which the catalyst is a mixture of the Group IIIB phosphate, monohydrogen phosphate and dihydrogen phosphate.

37. The process of claim 20 in which the catalyst is a mixture of the Group IIIB phosphate, monohydrogen phosphate and dihydrogen phosphate.

38. The process of claim 23 in which the catalyst is a mixture of the Group IIIB phosphate, monohydrogen phosphate and dihydrogen phosphate.

39. The process of claim 28 in which the catalyst is a mixture of the Group IIIB phosphate, monohydrogen phosphate and dihydrogen phosphate.

* * * * *